US010952604B2

United States Patent
Askarian et al.

(10) Patent No.: US 10,952,604 B2
(45) Date of Patent: Mar. 23, 2021

(54) DIAGNOSTIC TOOL FOR EYE DISEASE DETECTION USING SMARTPHONE

(71) Applicant: Texas Tech University System, Lubbock, TX (US)

(72) Inventors: Behnam Askarian, Lubbock, TX (US); Jo Woon Chong, Lubbock, TX (US); Fatemehsadat Tabei, Lubbock, TX (US)

(73) Assignee: TEXAS TECH UNIVERSITY SYSTEM, Lubbock, TX (US)

( * ) Notice: Subject to any disclaimer, the term of this patent is extended or adjusted under 35 U.S.C. 154(b) by 198 days.

(21) Appl. No.: 16/294,902

(22) Filed: Mar. 6, 2019

(65) Prior Publication Data

US 2019/0274536 A1     Sep. 12, 2019

Related U.S. Application Data

(60) Provisional application No. 62/639,313, filed on Mar. 6, 2018.

(51) Int. Cl.
| | |
|---|---|
| *A61B 3/00* | (2006.01) |
| *G06T 7/00* | (2017.01) |
| *G06K 9/62* | (2006.01) |
| *G06T 7/13* | (2017.01) |
| *A61B 3/107* | (2006.01) |
| *A61B 3/14* | (2006.01) |

(52) U.S. Cl.
CPC ............ *A61B 3/0025* (2013.01); *A61B 3/107* (2013.01); *A61B 3/14* (2013.01); *G06K 9/6262* (2013.01); *G06T 7/0016* (2013.01); *G06T 7/13* (2017.01); *G06T 2207/20021* (2013.01); *G06T 2207/20036* (2013.01); *G06T 2207/20081* (2013.01); *G06T 2207/30041* (2013.01)

(58) Field of Classification Search
CPC ......... A61B 3/0025; A61B 3/107; A61B 3/14; G06T 7/0016; G06T 7/13; G06T 2207/20021; G06T 2207/30041; G06T 2207/20081; G06T 2207/20036; G06T 7/12; G06K 9/6262; G06K 2209/05; G06K 9/6273; G06K 9/4628; G06K 9/3241
USPC ....................................................... 351/206
See application file for complete search history.

(56) References Cited

U.S. PATENT DOCUMENTS

2013/0235346 A1* 9/2013 Huang ................... A61B 3/152
                                                                    351/208

* cited by examiner

*Primary Examiner* — Mohammed A Hasan
(74) *Attorney, Agent, or Firm* — Dickinson Wright PLLC; Kristopher Lance Anderson

(57) ABSTRACT

Diagnostic tool for eye disease detection using a smartphone. At least some of the example embodiments are methods including capturing, by way of a camera lens on a device, an image of an eye to create a raw specimen; processing the raw specimen to create a processes specimen; performing edge detection on the processed specimen to detect a boundary of a cornea; extracting a region of interest of the cornea; identifying a boundary of the region of interest using a boundary tracing technique to identify a second boundary; analyzing the second boundary of the region of interest, by measuring a slope of the second boundary; and classifying the region of interest as including an eye disease, based on the analyzing the second boundary.

20 Claims, 9 Drawing Sheets

|  | | Predicted | | | | |
|---|---|---|---|---|---|---|
|  | | Mild | Moderate | Advanced | Severe | Normal |
| Actual class | Mild | 10 | 2 | 0 | 0 | 8 |
|  | Moderate | 7 | 27 | 6 | 0 | 0 |
|  | Advanced | 0 | 5 | 34 | 1 | 0 |
|  | Severe | 0 | 0 | 1 | 19 | 0 |
|  | Normal | 57 | 16 | 2 | 0 | 65 |

*FIG. 6*

|  | | Predicted | | | | |
|---|---|---|---|---|---|---|
|  | | Mild | Moderate | Advanced | Severe | Normal |
| Actual class | Mild | 1 | 0 | 0 | 0 | 0 |
|  | Moderate | 1 | 1 | 0 | 0 | 0 |
|  | Advanced | 0 | 0 | 2 | 0 | 0 |
|  | Severe | 0 | 0 | 0 | 1 | 0 |
|  | Normal | 6 | 1 | 0 | 0 | 7 |

*FIG. 7*

DIAGNOSTIC TOOL FOR EYE DISEASE DETECTION USING SMARTPHONE

CROSS-REFERENCE TO RELATED APPLICATIONS

This application claims the benefit of U.S. Provisional Application Ser. No. 62/639,313 filed Mar. 6, 2018 titled "Diagnostic Tool For Eye Disease Detection Using Smartphone". The provisional application is incorporated by reference herein as if reproduced in full below.

BACKGROUND

All too often, as we age, our eyesight deteriorates. According to the Centers for Disease Control and Prevention (CDC), in a population of Americans over 40, 16% have cataracts and 2% have glaucoma. A more rare disease is keratoconus, which is an irregularity of the shape of the cornea. Keratoconus is treatable in early stages, however, keratoconus is often detected using bulky and expensive machines operated by trained technicians. For example, eye diseases can be detected by OCT, UBM, corneal topography, Scheimpflug camera, laser interferometry, and computerized videokeratoscopy. As topography devices are large, expensive, and not portable, keratoconus may not be detected in early stages, and therefore go untreated, in a poor population or a population that lacks access to healthcare.

BRIEF DESCRIPTION OF THE DRAWINGS

For a detailed description of example embodiments, reference will now be made to the accompanying drawings in which:

FIG. 6 shows a chart showing keratoconus detection accuracies, in accordance with at least some embodiments.

FIG. 7 shows a chart showing keratoconus detection accuracies, in accordance with at least some embodiments.

DEFINITIONS

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

"Controller" shall mean individual circuit components on a substrate, an application specific integrated circuit (ASIC) constructed on a substrate, a microcontroller constructed on a substrate (with controlling software stored on the substrate), or combinations thereof, configured to read signals and take action responsive to such signals.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Often, eye diseases such as keratoconus is detected in clinics with ophthalmic devices, which are large, expensive, not portable, and are operated by trained technicians. At least some of the example embodiments are directed to a diagnostic tool for eye disease detection using a smartphone. More particularly, an affordable and easy-to-use diagnostic tool for eye disease detection, such as an eye disease detection application operating on a smart phone. The eye disease detection application is configured to detect diseases such as keratoconus, cataract, glaucoma, and strabismus. The specification now turns to an example current sense system in accordance with example embodiments.

Figure 1A:
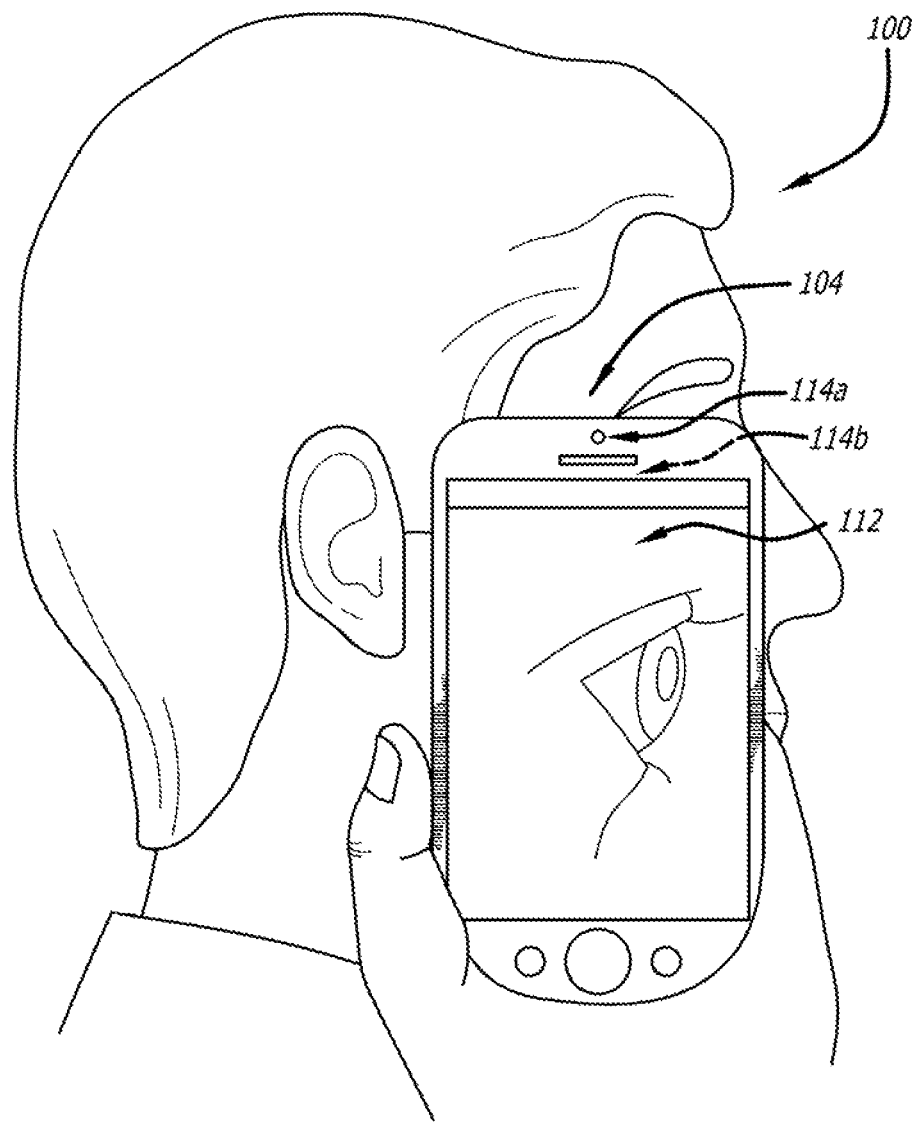
FIG. 1A shows a front elevation view of a smart phone capturing a specimen, in accordance with at least some embodiments.

FIG. 1A shows a front elevation view of a device 102 (e.g., a smart phone), in an environment 100, in accordance with at least some embodiments. In particular, the device 102, is positioned to capture a profile view of an eye. As used herein, a profile view of the eye is defined as the perspective of the eye resulting from viewing or capturing an image of the eye from a position that is 90 degrees from either an optical axis of the eye or a line of sight of the eye. The human eye includes the cornea (transparent layer), the crystalline lens, and the iris. As used herein, the optical axis of the eye is defined as the line joining the centers of curvature of all the optical surfaces. The line of sight is defined as the ray that passes through the center of the entrance pupil and strikes the center of the fovea.

In various embodiments, the device 102 is configured detect the presence of an eye disease in the eye 104. For example, the device 102 is configured to capture an image of the eye 104 as a raw specimen, process the raw specimen to create a processed specimen, analyze the specimen and determine whether the specimen includes an image of an eye with an eye disease such as keratoconus.

Figure 1B:
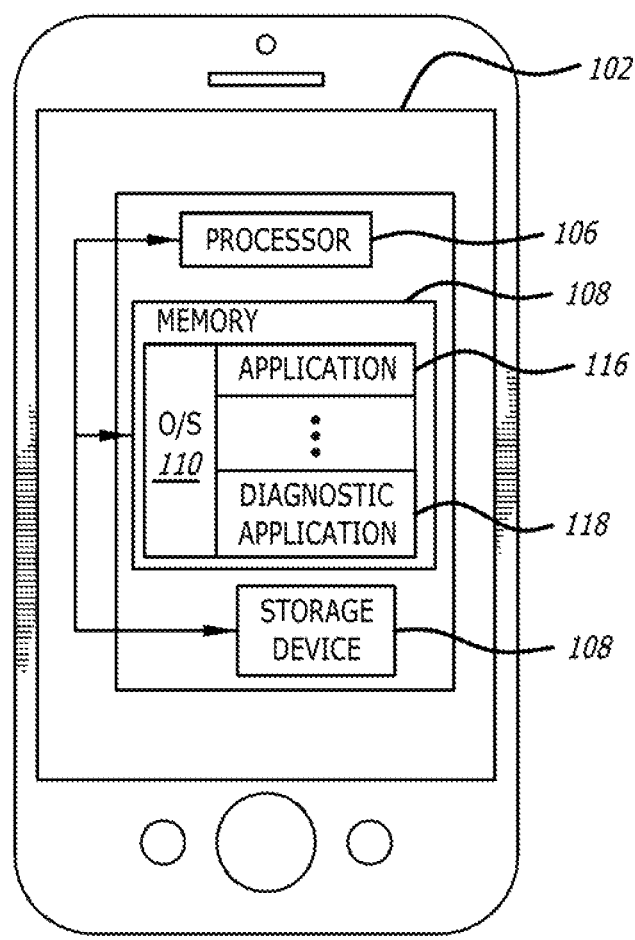
FIG. 1B shows a block diagram view of the smart phone in accordance with at least some embodiments.

As shown in FIG. 1B, the device 102 can include at least one processor 106, at least one memory 108, and at least one storage device 108. According to some embodiments, the device 102 can represent any form of a computing device, e.g., a smartphone, a tablet, a laptop, and a desktop computing device.

According to some embodiments, the processor 106 can be configured to operate in conjunction with, the memory 108 and the storage device 108, to enable the device 102 to implement the various techniques to detect eye disease, set forth in this disclosure. According to some embodiments, the storage device 108 can represent a storage device that is accessible to the device 102, e.g., a hard drive, a solid-state drive (SSD), a mass storage device, and a remote storage device.

In some embodiments, the storage device 108 is a storage device internal to the device 102. The storage device 108 can be configured to store an operating system (OS) file system volume that is mounted at the device 102, where the OS file system volume includes an OS 110 that is compatible with the device 102. Examples of the OS 110, specifically where the device 102 is a smartphone includes Google Android®, Research in Motion's BlackBerry OS, Microsoft's Windows Phone® OS, and Apple iOS®.

Still referring to FIG. 1B, the OS 110 enables a variety of processes to execute on the device 102, e.g., OS daemons, native OS applications (e.g., application 116), native OS applications, user applications, and the like. For example, the application 116 can be a photo application, a mail application, a camera application, and a contacts application. Additionally, the OS 110 enables the diagnostic application 118 to execute on the device 102.

In some embodiments, the device 102 comprises a display screen 112 configured to display data received from the processor 106, and a camera lens disposed on the first side of the device 114a and a separate camera lens disposed on the back side of the device 114b. As shown in FIG. 1A, the raw specimen is captured by way of the camera lens 114b disposed on the back side of the device from a position that captures the profile view of the eye. The raw specimen can be captured by one or more applications executing on the device 102, such as a camera application or the diagnostic application 118. For example, the raw specimen can be captured using a camera application native to the OS 110 or separately installed from an application store. In one embodiment, the raw specimen is captured by the camera application and sent to diagnostic application 118. In other embodiments, the diagnostic application 118 is configured to render for display a graphical user interface similar to one displayed by the camera application, and which enables a user to capture the profile view of the eye using the camera lens 114b.

The diagnostic application 118 is further configured to diagnose eye diseases detected within the captured image of the profile view of the eye. In particular, the diagnostic application 118 is configured to diagnose eye diseases without the use of an additional adaptor lenses, gadgets, or topographer tools. That is, the diagnostic application 118 utilizes the hardware that is part of (e.g., on the device when shipped from the factory) of the device 102.

The example method illustrated herein is used to detect keratoconus. Presently, keratoconus is detected by one of the following laboratory or clinical methods: optical coherence tomography (OCT), ultrasound bio-microscopy (UBM), corneal topography, Scheimpflug camera, and laser interferometry. These methods include projecting light circles (known as Placido discs) on the surface of the cornea, and measuring the differences between the reference and reflected circles. Accordingly, the corneal topography detects any irregularities in a cornea's shape.

Figure 2A:
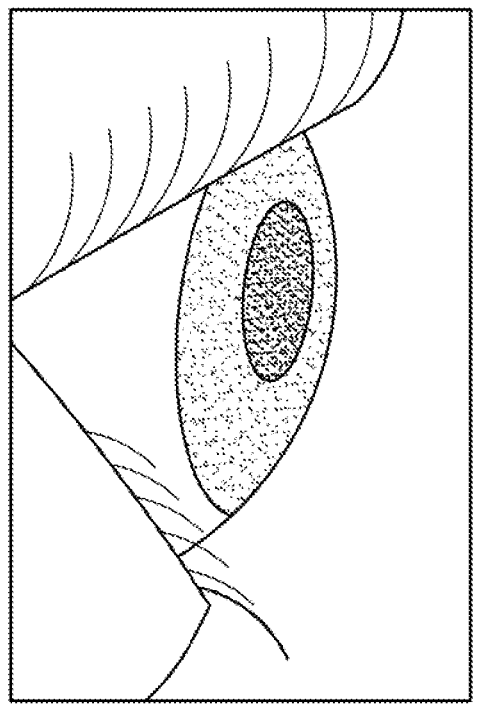
FIG. 2A shows an example processed specimen, in accordance with at least some embodiment.
Figure 2B:
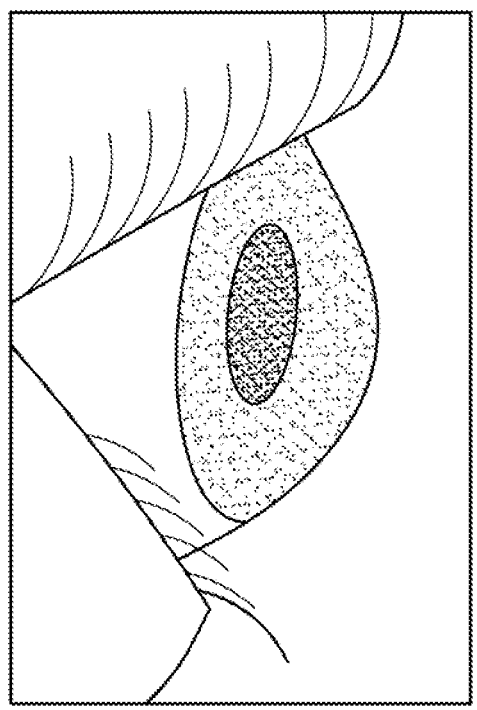
FIG. 2B shows an example processed specimen, in accordance with at least some embodiments.

As is known, symptoms of keratoconus include a thinner middle cornea which bulges outward gradually, causing the cornea to change shape into a cone-shaped cornea (as can be seen in the processed specimen in FIG. 2B). Depending on the thickness, steepness, and morphology of the cornea, keratoconus is classified into four stages: mild, moderate, advanced, and severe stages. If caught in the early stages, keratoconus can be effectively treated by treatments including corneal collagen cross-linking.

However, such methods use large and expensive equipment. Accordingly, cost and access to affordable healthcare can be a barrier to early detection of keratoconus. The described diagnostic application 118 provides a low-cost method for detecting keratoconus that uses the device 102 and does not additionally require adaptor lenses, gadgets, or topographer tools.

In particular, the disclosed methods implemented by the diagnostic application 118, find the axial of the cornea curve where the axial is the perpendicular axis to the axis which the cornea lies on. Initially a captured image undergoes a binarization process (e.g., converted to gray scale). After binarization, the diagnostic application 118 can apply various algorithms to close discontinuous objects (e.g., using morphological dilation) and extracts connected structures into a single region of interest (ROI) using the connected components approach based on a region growing algorithm. The diagnostic application 118 can fill holes which might be present in the object by extending the ROI by a one-pixel wide border to separate objects from the ROI margin. Next, the diagnostic application 118 applies a flood filling algorithm to assign an arbitrary intensity value to all pixels surrounding the object. In a final step, the diagnostic application 118 assigns an object intensity value to all pixels that do not correspond to the arbitrary intensity value. The foregoing steps are considered preprocessing steps for the purposes of this discussion.

After preprocessing an object (e.g., an image of an eye), all single objects are stored in a dataset that is used in the successive parameterization and classification steps. The diagnostic application 118 can perform a classification step by using machine learning techniques such as convolutional neural network (CNN). Turning now to FIGS. 2A and 2B an example method of diagnosing keratoconus is discussed.

In FIGS. 2A and 2B, example images are shown in which the diagnostic application 118 has captured an image of the eye (using camera lens 114b), as raw specimens, and additionally processed the image to create respective processed specimens. In one example, the device 102 is an iPhone 5S® with an 8-megapixel (3264×2448) primary camera, where the primary camera is configured to capture the raw specimen using the maximum resolution when capturing the raw specimen.

In particular, FIG. 2A illustrates a processed specimen which captures an image of an eye that does not have an eye disease, and FIG. 2B illustrates a processed specimen which captures an image of an eye that has keratoconus. As previously described, keratoconus causes the cornea to change shape into a cone-shaped cornea (illustrated in FIG. 2B). The occurrence of a cone-shaped cornea results in a weakening of the cornea's refractive power, since the cone-shape interferes with the cornea's ability to refract, and the cornea is responsible for around 70% of the eye's refractive power. Changes in the eye's refractive power results in nearsightedness, astigmatism, and blurred vision. The ability to detect keratoconus in the early stages using a low cost solution can make it possible for an individual to seek treatment, as keratoconus is treatable in early stages.

Still referring to FIGS. 2A and 2B, the diagnostic application 118 captures the profile view of the eye to create a raw specimen. The raw specimen can include the image of the eye including the eye, sclera, an eye lid, eye lashes, and skin surrounding the eye. Various method of processing the raw specimen implemented by the diagnostic application 118 include cropping the image such that all objects are cropped except for the cornea, implementing background reduction techniques, applying edge detection techniques, and rotating the image by 90 degrees. Specifically, in FIGS. 2A and 2B, the raw specimens have been initially processed by the diagnostic application 118, by cropping all objects except for the cornea in each respective image.

FIGS. 3A, 3B, 3C, and 3D illustrate additionally processed specimens. Additional processing techniques illustrated in FIGS. 3A, 3B, 3C, and 3D include background reduction techniques, applying edge detection techniques, closing structures, identifying a region of interest ("ROI"), boundary tracing, and filling holes.

Figure 3A:
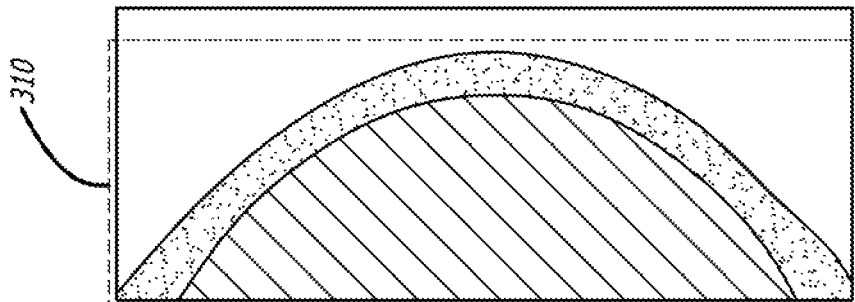
FIG. 3A shows an example processed specimen, in accordance with at least some embodiments.
Figure 3B:
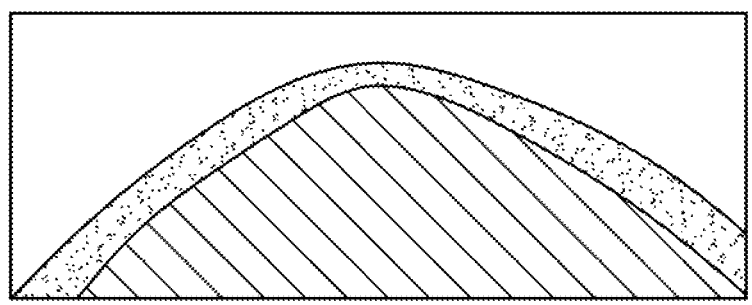
FIG. 3B shows an example processed specimen, in accordance with at least some embodiments.

In one example, the processed specimens in FIGS. 2A and 2B are initially converted to grayscale images to create the processed specimens in FIGS. 3A and 3B, respectively. In various embodiments, the grayscale images are binary images upon which the diagnostic application 118 performs additional processing that includes edge detection algorithms and morphological dilation.

The diagnostic application 118 can use various edge detection techniques (e.g., the Canny algorithm), to identify a boundary of the cornea, such as boundary 302 and boundary 304. In some embodiments, the Canny algorithm is an edge detection algorithm which uses a multi stage algorithm for detecting the edges in a wide range of images. In this example, the Canny algorithm is used to detect the edges and morphology of the cornea.

For example, the diagnostic application 118 applies edge detection techniques to the processed image in FIG. 3a to determine a boundary 302 of the cornea. Additionally, the diagnostic application 118 applies edge detection techniques to the processed image in FIG. 3b to determine a boundary 304 of the cornea. Additional details of example edge detection techniques can be found here: Canny, L. "A Computational Approach to Edge Detection," IEEE Transactions on Pattern Analysis and Machine Intelligence, PAMI-8(6), 679-698 (1986), which is hereby incorporated by reference herein.

Still referring to FIGS. 3A-3D, additional processing performed by the diagnostic application 118 include morphological dilation to generate a smooth edge of the boundary. Any dilation algorithm can be used (e.g., morphological dilation) that closes gaps/fills holes in discontinuous objects to produce a more connected structure. Morphological dilation is a morphological operation implemented on binary images, such as processed specimens in FIGS. 3C and 3D, where dilations add pixels to the pixels in the identified boundary (e.g., boundaries 302 or 304) to generate a smoother boundary.

Additional processing performed by the diagnostic application 118 also includes extracting or identifying a region of interest ("ROI"). With reference to an image of an eye, the ROI can identify various parts of the eye. In the example of detecting keratoconus, an example region of interest 310 (FIG. 3A) is the outer part of the eye. In one example, the diagnostic application 118 extends the ROI by a one-pixel wide border to separate objects from the ROI margin (e.g., by applying morphological dilation).

The various techniques applied by the diagnostic application 118, including the edge detection techniques and morphological dilation, can be used to identify a thickness, steepness, and morphology of the cornea.

Figure 3C:
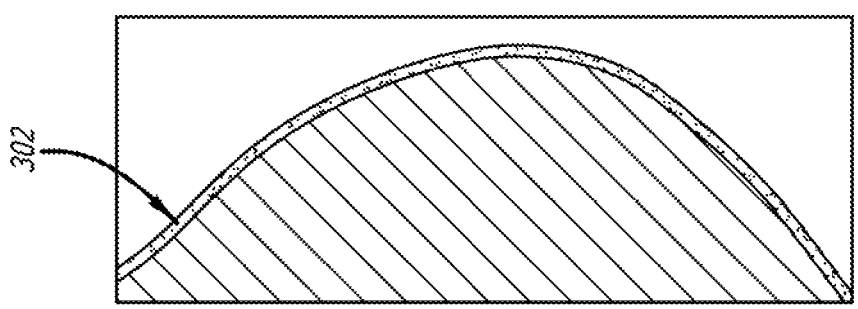
FIG. 3C shows an example processed specimen, in accordance with at least some embodiments.
Figure 3D:
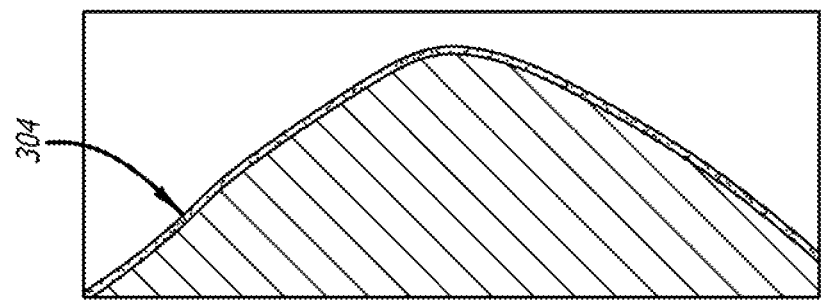
FIG. 3D shows an example processed specimen, in accordance with at least some embodiments.
Figure 4A:
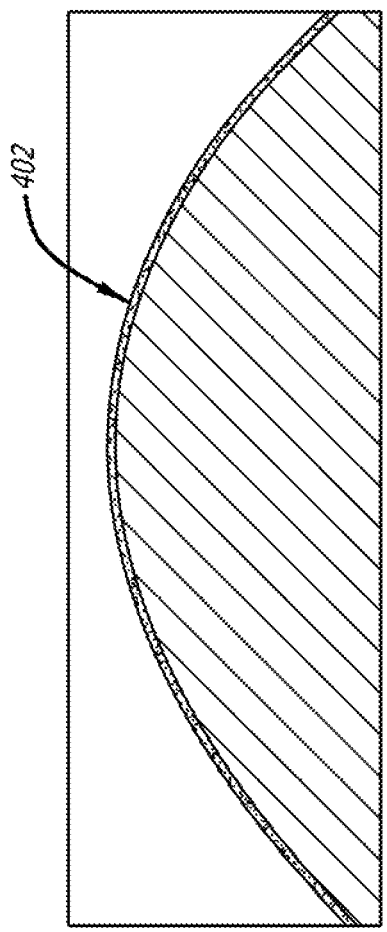
FIG. 4A shows an example processed specimen, in accordance with at least some embodiments.
Figure 4B:
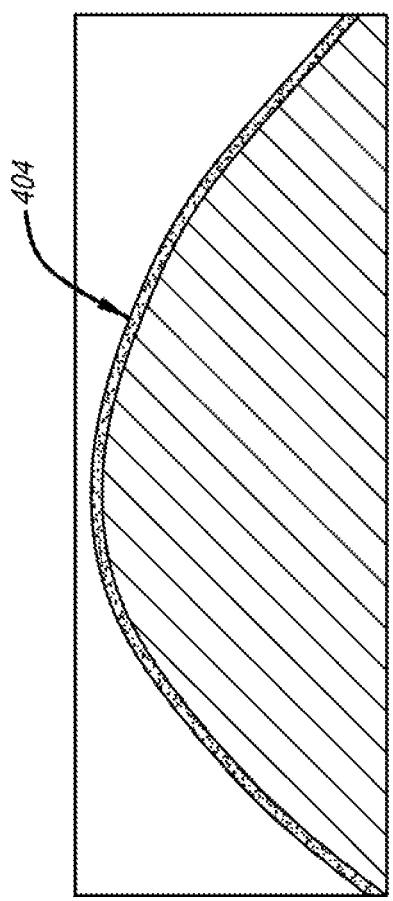
FIG. 4B shows an example processed specimen, in accordance with at least some embodiments.

As shown in FIGS. 4A and 4B, the diagnostic application 118 rotates the processed specimens in FIGS. 3C and 3D by 90 degrees. Specifically, the processed specimen shown in FIG. 3C (e.g., a normal eye) is rotated by 90 degrees to create the processed specimen shown in FIG. 4A and the processed specimen shown in FIG. 3D (e.g., an eye with keratoconus) is rotated by 90 degrees to create the processed specimen shown in FIG. 4B. In various embodiments, the diagnostic application 118 can identify a boundary of the region of interest using a boundary tracing technique to identify a final or second boundary of the region of interest (e.g., boundaries 402 and 404).

Next, the processed specimens in FIGS. 4A and 4B, and more specifically, the second boundary of the region of interest is analyzed and classified by the diagnostic application 118 (described in further detail in FIGS. 5A-5D).

Figure 5A:
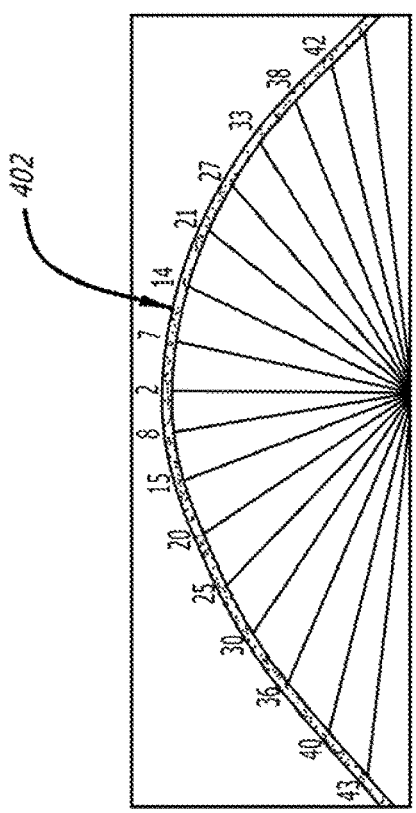
FIG. 5A shows a method of measuring a slope angle, in accordance with at least some embodiments.
Figure 5B:
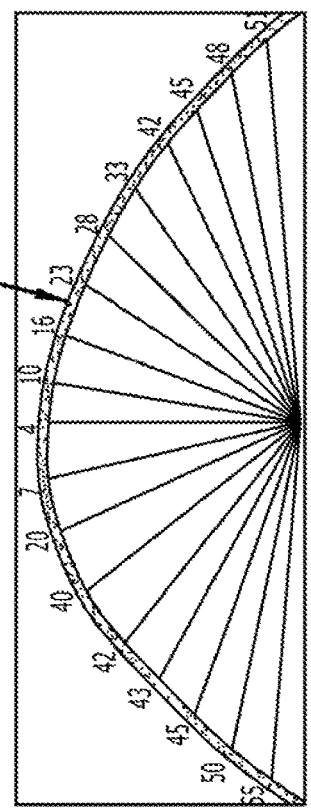
FIG. 5B shows a method of measuring a slope angle, in accordance with at least some embodiments.
Figure 5C:
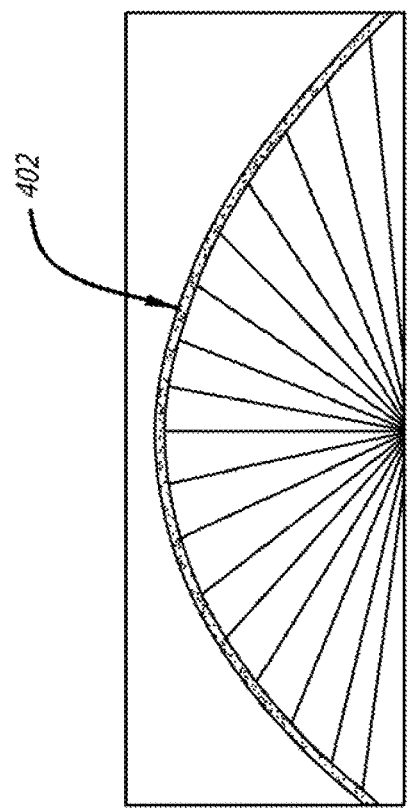
FIG. 5C shows a method of measuring a slope angle, in accordance with at least some embodiments.
Figure 5D:
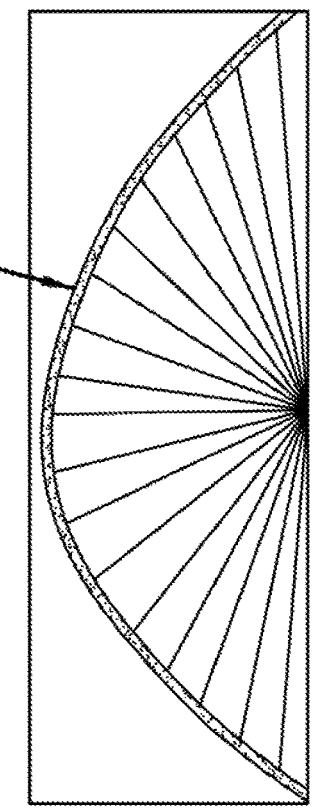
FIG. 5D shows a method of measuring a slope angle, in accordance with at least some embodiments.

In FIG. 5A the second boundary 402 is shown in FIGS. 5A and 5B (normal eye), while the second boundary 404 is shown in FIGS. 5C and 5D (eye with keratoconus). The diagnostic application 118 is configured to classify keratoconus eyes from normal eyes using the slope of corneal curvature.

In one embodiment, the diagnostic application 118 measures the slope angle of the corneal curvature at "N" different points (e.g., measuring points) where each of the points is separated by an interval value. In one example, the interval value defines a number of degrees separating each measuring point, in another example, the interval value defines an arc length. The foregoing examples of an interval value are not meant to be limiting and any type of measurement of distance can be used to define the interval value. In various embodiments, the interval value is a predefined value that can be provided by a programmer of the diagnostic application 118, or the interval value can be provided by a user (e.g., a physician using the application during an examination procedure).

In FIGS. 5A and 5C, the diagnostic application 118 is configured to measure the slope angle of the corneal curvature at 18 different points, and thus slope angles are sampled at every 10 degrees. The keratoconus eye has higher elevation and steeper curvature compared to a normal eye. Accordingly, as illustrated in FIGS. 5B and 5D (which respectively correspond to the second boundary 402 and 404), the corneal surface of the normal cornea has a round curvature and regular slope variation (FIG. 5B), while the corneal surface of the keratoconus eye has a cone shape with irregular slope variations (FIG. 5D).

In some embodiments, the slope of the curvature of the second boundary 404 is measured at every 10 degrees, and then the diagnostic application 118 is configured to use machine learning techniques such as convolutional neural network (CNN) to compare the measured slopes of curvature of the second boundary 404 with the training data.

FIGS. 6 and 7 shows charts comparing actual classification of keratoconus (actual class) and a diagnosis of keratoconus using methods described herein (predicted). In particular, data for the charts were collected using the medical history (topography) and ophthalmologists' diagnosis of 20 eyes from the Poostchi Eye Hospital from Shiraz University of Medical Sciences.

The methods disclosed herein were used on the 20 eyes, where various factors were changed when using the diagnostic application 118 including the distance between the eye and the device 102, as well as the brightness and saturation of the raw specimen (e.g., captured image). The exam, using, the diagnostic application 118 was used 20 times for the keratoconus eyes and 10 times for the normal eyes. As shown in FIGS. 6 and 7, the disclosed method detects the stages of keratoconus with the following accuracies: severe stage at 93%, advanced stage at 86%, moderate stage at 67%, and mild stage at 50%.

Figure 8:
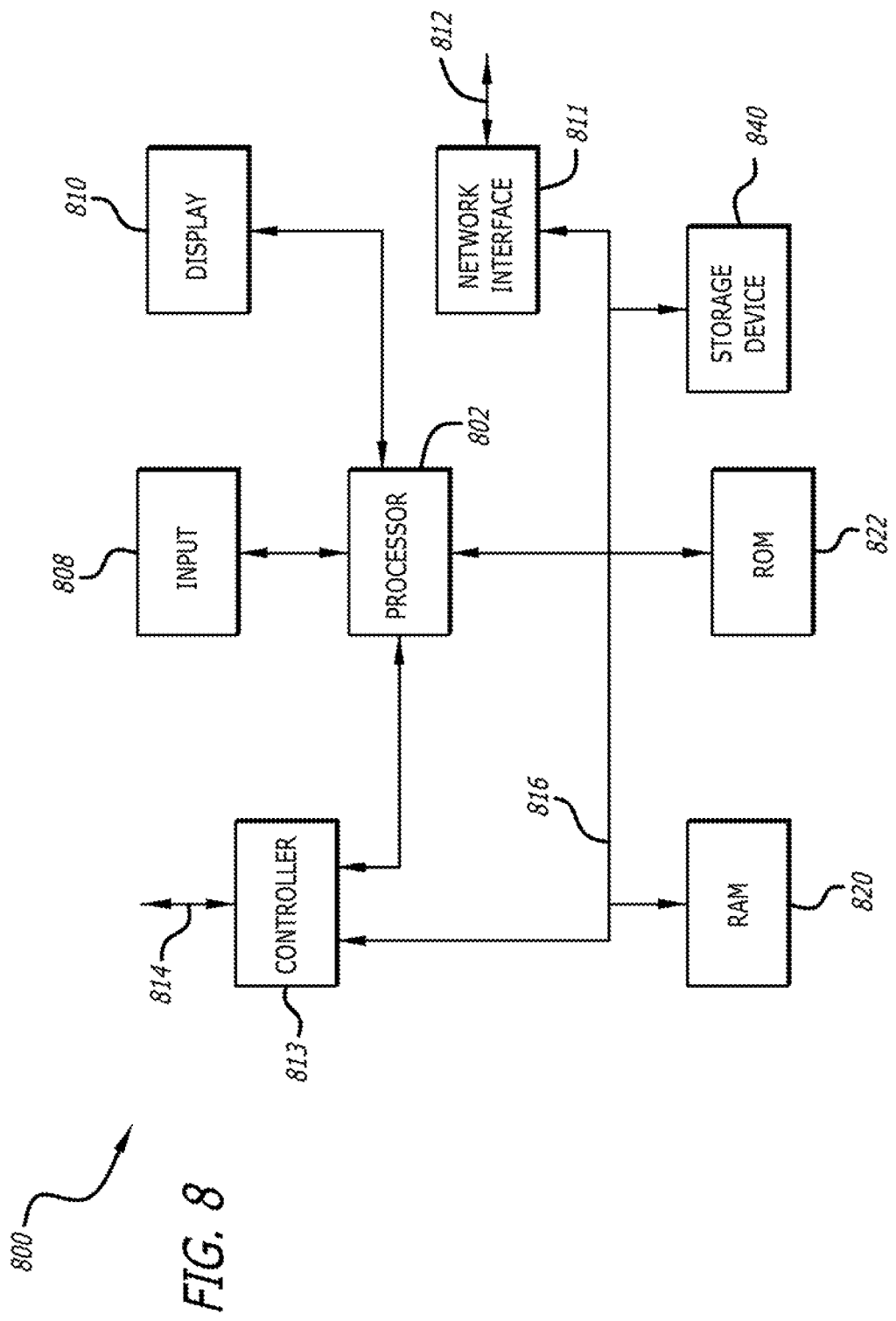
FIG. 8 shows a detailed view of a computing device that can represent the device of FIG. 1 used to implement the diagnostic tool described herein, in accordance with some embodiments.

FIG. 8 illustrates a detailed view of a computing device 800 that can represent the device 102 of FIG. 1 used to implement the various techniques described herein, according to some embodiments. As shown in FIG. 8, the computing device 800 can include a processor 802 that represents a microprocessor or controller for controlling the overall operation of the computing device 800. The computing device 800 can also include a user input device 808 that allows a user of the computing device 800 to interact with the computing device 800. For example, the user input device 808 can take a variety of forms, such as a button, keypad, dial, touch screen, audio input interface, visual/image capture input interface, input in the form of sensor data, and so on. Still further, the computing device 800 can include a display 810 that can be controlled by the processor 802 (e.g., via a graphics component) to display information to the user (e.g., display a raw or processed specimen). A data bus 816 can facilitate data transfer between at least a storage device 840, the processor 802, and a controller 813. The controller 813 can be used to interface with and control different equipment through an equipment control bus 814. The computing device 800 can also include a network/bus interface 811 that couples to a data link 812. In the case of a wireless connection, the network/bus interface 811 can include a wireless transceiver.

As noted above, the computing device 800 also includes the storage device 840, which can comprise a single disk or a collection of disks (e.g., hard drives). In some embodiments, storage device 840 can include flash memory, semiconductor (solid state) memory or the like. The computing device 800 can also include a Random-Access Memory (RAM) 820 and a Read-Only Memory (ROM) 822. The ROM 822 can store programs, utilities or processes to be executed in a non-volatile manner. The RAM 820 can provide volatile data storage, and stores instructions related to the operation of applications executing on the computing device 800.

Figure 9:
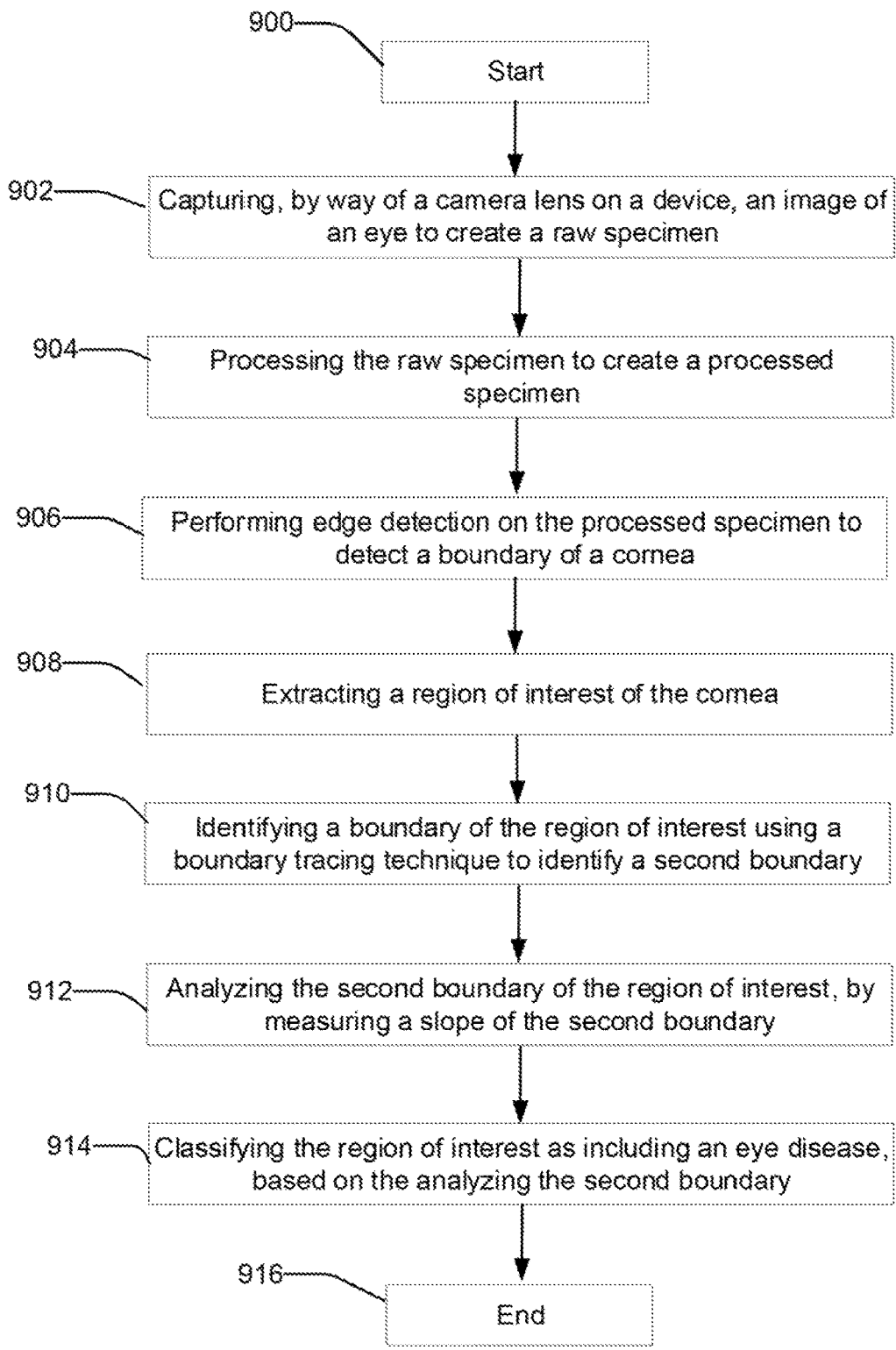
FIG. 9 shows a method, in accordance with some embodiments.

FIG. 9 is a method diagram in accordance with at least some embodiments, In particular, the method starts (block 900) and includes: capturing, by way of a camera lens on a device, an image of an eye to create a raw specimen (block 902); processing the raw specimen to create a processed specimen (block 904); performing edge detection on the processed specimen to detect a boundary of a cornea (block 906); extracting a region of interest of the cornea (block 908); identifying a boundary of the region of interest using a boundary tracing technique to identify a second boundary (block 910); analyzing the second boundary of the region of interest, by measuring a slope of the second boundary (block 912); and classifying the region of interest as including an eye disease, based on the analyzing the second boundary (block 914). Thereafter the method ends (block 916).

Accordingly, the described diagnostic application 118 provides a low-cost method for detecting keratoconus that uses the device 102 and does not additionally require adaptor lenses, gadgets, or topographer tools (e.g., Keratoscope, slit lamp, etc.).

In particular, the disclosed methods implemented by the diagnostic application 118, find the axial of the cornea curve where the axial is the perpendicular axis to the axis which the cornea lies on. Initially a captured image undergoes a binarization process (e.g., converted to gray scale). After binarization, the diagnostic application 118 can apply various algorithms to close discontinuous objects (e.g., using morphological dilation) and extracts connected structures into a single region of interest (ROI) using the connected components approach based on a region growing algorithm. The diagnostic application 118 can fill holes which might be present in the object by extending the ROI by a one-pixel wide border to separate objects from the ROI margin. Next, the diagnostic application 118 applies a flood filling algorithm to assign an arbitrary intensity value to all pixels surrounding the object. In a final step, the diagnostic application 118 assigns an object intensity value to all pixels that do not correspond to the arbitrary intensity value. The foregoing steps are considered preprocessing steps for the purposes of this discussion.

After preprocessing an object (e.g., an image of an eye), all single objects are stored in a dataset that is used in the successive parameterization and classification steps. The diagnostic application 118 can perform a classification step by using machine learning techniques such as convolutional neural network (CNN).

The described method does not require image normalization as an image (e.g., raw specimen) gathered by the device 102 is large enough (e.g., contains enough pixels, a large enough resolution), to measure the curvature of the cornea. The curvature and the morphological properties do not change by normalization. Thus, the described methods do not entail resizing the image to a certain size, as the methods described herein work with images of any size.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. A method of screening for eye disease, comprising:
capturing, by way of a camera lens on a device, an image of an eye to create a raw specimen;
processing the raw specimen to create a processed specimen;
performing edge detection on the processed specimen to detect a boundary of a cornea;
extracting a region of interest of the cornea;
identifying a boundary of the region of interest using a boundary tracing technique to identify a second boundary;
analyzing the second boundary of the region of interest, by measuring a slope of the second boundary; and
classifying the region of interest as including an eye disease, based on the analyzing the second boundary.

2. The method of claim 1, wherein the capturing further comprises, capturing a profile view of the eye.

3. The method of claim 1, wherein the eye disease is keratoconus and further wherein classifying the region of interest further comprises identifying at least one selected from the group consisting of: mild stage, moderate stage, advanced stage, and severe stage.

4. The method of claim 1, wherein processing the raw specimen further comprises cropping out portions of the image that include eyelashes and an eyelid to create a first processed specimen.

5. The method of claim 4, further comprising, rotating the first processed specimen by 90 degrees to create a second processed specimen.

6. The method of claim 1, wherein analyzing the second boundary of the region of interest further comprises:
defining an interval value;
dividing the secondary boundary into portions based on the interval value; and
measuring a slope of the secondary boundary at each of the portions to obtained measured slopes.

7. The method of claim 6, wherein classifying the region of interest further comprises:
comparing the measured slopes to training data; and
identifying a classification based on the comparing the measures slopes.

8. The method of claim 1, wherein performing edge detection further comprises applying a Canny algorithm.

9. The method of claim 1, wherein processing the raw specimen to create a processed specimen further comprises:
converting the raw specimen to a grayscale image; and
applying a morphological dilation to the grayscale image.

10. A device configured to detect an eye disease, comprising:
a processor;
a camera lens coupled to the processor; and
a memory coupled to the processor, the memory storing computer-readable instructions that are executable by the processor to cause a computer to execute operations comprising:
capturing, by way of the camera lens, an image of an eye to create a raw specimen;
processing, the raw specimen to create a processed specimen;
performing edge detection on the processed specimen to detect a boundary of a cornea;
extracting a region of interest of the cornea;
identifying a boundary of the region of interest using a boundary tracing technique to identify a second boundary;
analyzing the second boundary of the region of the interest, by measuring a slope of the second boundary; and
classifying the region of interest as including an eye disease, based on the analyzing the second boundary.

11. The device of claim 10, wherein the capturing further comprises, capturing a profile view of the eye.

12. The device of claim 10, wherein the eye disease is keratoconus and further wherein classifying the region of interest further comprises identifying at least one selected from the group consisting of: mold stage, moderate stage, advanced stage, and severe stage.

13. The device of claim 10, wherein processing the raw specimen further comprises cropping out portions of the image that include eyelashes and an eyelid to create a first processed specimen.

14. The device of claim 10, further comprising, rotating the first processed specimen by 90 degrees to create a second processed specimen.

15. The device of claim 10, wherein the memory stores computer-readable instructions that further cause the processor to:
define an interval value;
divide the secondary boundary into portions based on the interval value;
measure a slope of the secondary boundary at each of the portions to obtain measured slopes;
compare the measured slopes to training data; and
identify a classification based on the comparing the measured slopes.

16. A computer-readable storage media storing instructions that are executable by a processor to cause a computer to execute operations comprising:
capturing, by way of a camera lens on a device, an image of an eye to create a raw specimen;
processing the raw specimen to create a processed specimen;
performing edge detection on the processed specimen to detect a boundary of a cornea;
extracting a region of interest of the cornea;
identifying a boundary of the region of interest using a boundary tracing technique to identify a second boundary;
analyzing the second boundary of the region of interest, by measuring a slope of the second boundary; and
classifying the region of interest as including an eye disease, based on the analyzing the second boundary.

17. The computer-readable storage media of claim 16, wherein the capturing further comprises, capturing a profile view of the eye.

18. The computer-readable storage media of claim 16, wherein processing the raw specimen further comprises cropping out portions of the image that include eyelashes and an eyelid to create a first processed specimen.

19. The computer-readable storage media of claim 16, wherein performing edge detection further comprises applying a Canny algorithm.

20. The computer-readable storage media of claim 16, wherein processing the raw specimen to create a processed specimen further comprises:
converting the raw specimen to a grayscale image;
cropping out portions of the grayscale image that include eyelashes and an eyelid; and
applying a morphological dilation to the grayscale image.

* * * * *